United States Patent [19]

Matsumura et al.

[11]  4,198,481
[45]  Apr. 15, 1980

[54] PROCESS FOR THE PREPARATION OF 2-HYDROXYMETHYL-3,4,5-TRIHYDROXY PIPERIDINE

[75] Inventors: Shingo Matsumura, Kyoto; Hiroshi Enomoto, Nagaokakyo; Yoshiaki Aoyagi, Kyoto; Yoji Ezure, Otsu; Yoshiaki Yoshikuni, Kameoka; Masahiro Yagi, Kusatsu, all of Japan

[73] Assignee: Nippon Shinyaku Co., Ltd., Japan

[21] Appl. No.: 960,852

[22] Filed: Nov. 15, 1978

[30] Foreign Application Priority Data

Nov. 21, 1977 [JP] Japan .................................. 52-140126

[51] Int. Cl.$^2$ ............................................. C12D 13/02
[52] U.S. Cl. ..................................... 435/122; 435/899
[58] Field of Search ...................................... 195/80 R

[56] References Cited

PUBLICATIONS

Murai et al., Chemical Abstract, vol. 87, 141271x (1977).

Primary Examiner—Lionel M. Shapiro
Attorney, Agent, or Firm—Jacobs & Jacobs

[57] ABSTRACT

2-Hydroxymethyl-3,4,5-trihydroxy piperidine, or moranoline, is prepared by culturing a moranoline-producing strain of microorganism of the genus Streptomyces in an appropriate culture medium and thereafter isolating moranoline from the culture medium.

4 Claims, No Drawings

PROCESS FOR THE PREPARATION OF 2-HYDROXYMETHYL-3,4,5-TRIHYDROXY PIPERIDINE

DETAILED DESCRIPTION

The present invention relates to a process for preparing moranoline, a blood-sugar level lowering substance which chemically is 2-hydroxymethyl-3,4,5-trihydroxy piperidine, according to the fermentation method.

Moranoline, which has been proved to be of value as a blood-sugar level lowering substance, has heretofore been obtained by extraction of crude mulberry white bark, see e.g., Yagi et al., J. Ag. Chem. Soc. Japan, 50, 571 (1976), and U.S. Pat. No. 4,065,562.

It has now been discovered strains of microorganism belonging to the genus Streptomyces produce moranoline. Any of moranoline-producing strains belonging to the genus Streptomyces can be used. As a typical instance, there can be mentioned strain SEN-158 separated from soils collected in Sapporo City, and identified as belonging to *Streptomyces lavendulae*. "*Streptomyces lavendulae* SEN-158" is deposited with the Fermentation Research Institute of Agency of Industrial Science and Technology under deposition number FERM-No. 4301 and at the American Type Culture Collection (ATCC No. 31434).

Determination of microbiological properties was carried out according to procedures of the International Streptomyces Project (I.S.P.) [see E. B. Shirling et al., Intern. J. Systematic Bacteriol., 16 (3), 313–340 (1966)]. Culture media disclosed in this reference and "Industrial Examination Standards, Applied Microorganism Industry" and S. A. Waksman, The Actinomycetes, 2, 1961 were employed. Hues are described according to "Color Harmony Manual" of Container Corporation of America, and additional comments are added according to need.

(1) Description of the Moranoline-producing Strain (a) Morphological characteristics:

Spores were produced very abundantly on the aerial mycelia under favorable conditions. The spores are cylindrical $[(0.5-0.7)\mu \times (0.7-1.0)\mu]$. The surface of the spores observed under the electron microscope appears smooth.

Under a microscopic observation, hooked, looped and curled spore chains are observed at the top of the long aerial hyphae. The strain, therefore, following the classification of I.S.P., falls in section Rerinaculiaperti. More than 10 spores per chain are observed. Usually a few turns of spirals and greatly extended (primitive) spirals are also observed. Fragmentation of the substrate mycelia is not observed. This morphology described above is seen on salts-starch agar, oatmeal agar and glycerol-asparagine agar. On yeast-malt agar straight spore chains are abundant but loops, hooks and curls are also observed.

(b) Color of colony:

Aerial mass color in the red color series (Tresner-Backus Color Wheels) on yeast-malt agar, glycerolasparagine agar, salts-starch agar and oatmeal agar. Aerial mass color is white early in the development of the culture and later becomes 5ec-6ec (lavender) to 5ge (light greyish reddish brown).

(c) Reverse side of colony:

No distinctive pigment is produced. The growth is light brown on yeast-malt agar, colorless to pale brown on oatmeal agar and colorless to greyish white to pale grey on salts-starch agar and glycerol-asparagine agar. The pigments are not pH indicators.

(d) Color in medium (soluble pigment):

Melanoid pigment is formed in peptone-yeast iron agar. No distinctive pigment is observed except pale or light brown in yeast-malt agar. The pigments are not pH indicators.

(e) Carbon utilization:

Saccharides described in I.S.P.: D-glucose is utilized, but L-arabinose, sucrose, D-xylose, D-fructose, raffinose, L-insitol, D-mannitol and rhamnose are not utilized.

Other saccharides: Mannose, maltose and salicin are utilized but lactose, galactose and inulin are not utilized.

(II) Other Properties.

(a) Cultural characteristics (incubation 14 days, at 27° C.):

| Culture Medium | Growth | Aerial Mycelia Formation | Aerial Mycelia Color | Color of Substrate Mycelia | Soluble Pigment |
|---|---|---|---|---|---|
| sucrose-nitrate agar | scanty | scanty | white | colorless, transparent | none |
| glycerin-nitrate agar | good | moderate | white | colorless to pale brown | none |
| glycerin-asparagine agar | good | good | lavender (5ec) to light greyish reddish brown (5ge) | colorless to greyish | none |
| glucose-asparagine agar | good | good | lavender to light greyish reddish brown (5ge) | colorless to greyish white | none |
| salts-starch agar | good | good | lavender to greyish yellowish pink (5dc) | colorless to greyish white | none |
| tyrosine agar | good | good | greyish yellowish pink (5dc) | greyish white | none |
| nutrient agar | good | scanty | white | pale brown | pale brown |
| oatmeal agar | good | good | greyish red (5dc - 5ge) | colorless to pale brown | none |
| yeast-malt agar | good | good | lavender to greyish red | brown | pale brown |
| peptone-yeast-iron agar | good | none | — | reddish brownish black | dark brown to black |
| Emerson's agar | good | scanty | white | pale brown | brown |
| potato slice | good | none | — | blackish brown | blackish brown |

Cultural characteristics on other media:

Glucose-pepton-gelatin culture medium: good growth, lavender aerial mycelium, pale brown vegetative mycelium, brown to blackish brown soluble pigment, gelatin weakly liquefied Cellulose: scanty growth on either Czapek's nitrate solution or Czapek's ammonium chloride solution Tryptone-yeast extract broth: good growth, light brown (or blackish brown) soluble pigment (b) Biochemical properties:
(1) Gelatin liquefaction: positive (weak)
(2) Nitrate reduction: positive (weak)
(3) Hydrolysis of starch: positive
(4) Milk coagulation: negative
(5) Milk peptonization: positive (weak)
(6) Production of hydrogen sulfide: negative
(7) Production of melanoid pigment: positive
(8) Tyrosinase: negative
(9) Growth temperature: Experiments were conducted at 5, 10, 13, 17, 22, 26, 30, 34, 37–38, 42, 46 and 50° C. No growth was observed below 10° C. or above 42° C. At 13 and 37°–38° C., the growth was scanty, but at other temperatures the growth was good. The optimum temperature was found to be about 26° C.
(10) Growth pH range: Growth was observed at a pH of 4.5 to 9.0, and the optimum pH was found to be in the range of from 6 to 7.5.
(11) Cellulase: negative From the microbiological properties, described above, it was confirmed that the strain (SEN-158) used in the present invention belongs to the genus Streptomyces. The present strain is mainly characterized in that it has aerial mycelium of the red color series (lavender) and has the morphological characteristics of the retinaculiaperti type, the spore surface is smooth, and the color of the substrate mycelium and the soluble pigment is not distinctive. Based on these characteristic properties, the present strain was examined in the light of teachings of such literature as E. B. Shirling and D. Gottlieb, Intern. J. Systematic Bacteriol., 18 (2), 69–189 (1968), 18 (4), 279–392 (1968), 19 (4), 391–512 (1969) and 22 (4), 265–394 (1972), and S. A. Waksman, The Actinomycetes, 2 (1961). As a result, the present strain was identified as *Streptomyces lavendulae.*

Since it was found that the strain SEN-158 had such a valuable characteristic that it produces a blood-sugar level lowering substance, moranoline, the strain was named "*Streptomyces lavendulae* SEN-158" for discrimination from known strains.

Not only the above-mentioned *Streptomyces lavendulae* and mutants thereof formed by mutation of said strain but also other moranoline-producing strains belonging to the genus Streptomyces can be used in the present invention.

In practicing the present invention, *Streptomyces lavendulae* SEN-158 is cultured according to methods customarily utilized for culturing microorganisms. As the carbon source, glucose, starch, glycerin and the like can be used, and as the nitrogen source, soybean powder, peptone, meat extract, corn steep liquor and the like can be used. When an appropriate amount of sodium chloride, potassium chloride, ammonium chloride, calcium carbonate or the like is added to the culture medium, good results can be obtained. Further, minute amounts of iron sulfate, magnesium sulfate and the like may be added. The culturing can be carried out according to any of the stationary culture method, the shaking culture method and the submerged agitation aerated culture method. The submerged agitation aerated culture method is most preferred. When the culturing is conducted at 22° to 30° C., preferably 25° to 27° C., at a pH of 6 to 8 for 48 to 72 hours, moranoline is produced in the culture medium.

For extraction and isolation of moranoline from the broth, various methods customarily used for extraction and purification of water-soluble substances can be adopted. For example, adsorption methods using active carbon, ion exchange methods, chromatographical fractionation using columns of, for example, a polyamide, sephadex, cellulose or silica gel or countercurrent distribution can be used for extraction, separation and purification of moranoline. Among them, an ion exchange method or fractionation method using active carbon is especially preferred.

The present invention can be described in detail by the following example.

EXAMPLE

In a 500 ml capacity Erlenmeyer flask was charged 200 ml of a culture medium containing 1% of glucose, 0.5% of meat extract, 0.5% of peptone, 0.5% of sodium chloride and 0.3% of calcium carbonate and having a pH of 7. The culture medium was sterilized according to customary procedures, and then inoculated with several platinum loops of spores of *Streptomyces lavendulae* SEN-158 collected from a slant culture. Culturing was conducted at 28° C. for 3 days under shaking at 200 rpm. Then, 7 l of a culture medium comprising 2% of starch, 1% of soybean powder, 0.05% of potassium chloride, 0.05% of magnesium sulfate (heptahydrate), 0.5% of sodium chloride, 0.2% of sodium nitrate and 0.35% of calcium carbonate, which was charged in a 14-liter capacity jar fermentor, was inoculated with the above mentioned precultured medium. Culturing was conducted at 28° C. for 48 to 72 hours at an aeration rate of 6 to 7 l/min. and an agitation vane rotation rate of 300 rpm.

Then, 3 kg of High-Flow Super-Cell was added to 12 l of the obtained culture medium and the culture medium was filtered. To the filtrate was added 4 l of methanol, and 500 g of active carbon (active carbon powder of the special grade manufactured by Wako Junyaku) was added and the mixture was agitated for 30 minutes. The active carbon was separated by filtration, and the filtrate was passed through a column packed with 2 l of an ion exchange resin [Dowex 1×2(OH$^-$type)]. The effluent was passed through a column packed with 500 ml of an ion exchange resin [Dowex 50W×4 (H$^+$type)]. The column was then washed with water and the adsorbed substance was dissolved out by 0.5% aqueous ammonia. The eluate was dried to solid under reduced pressure. The residual solid was dissolved in 100 ml of water, and 2 g of active carbon was added to the solution and the mixture was agitated for 30 minutes. The active carbon was removed by filtration, and the filtrate was passed through a column packed with 200 ml of Dowex 1×2(OH$^-$type) and the effluent was passed through a column packed with 200 ml of Dowex 50W×4(H$^+$type). The column was washed with water and the adsorbed substance was dissolved out with 0.28% aqueous ammonia. The eluate was dried to solid under reduced pressure, and the residual solid was dissolved in a small amount of methanol. When the solution was allowed to stand, a colorless crystal of moranoline was precipitated. The yield was 600 mg. Moranoline was obtained in the form of a colorless crystal stable to acids and alkalis, easily soluble in water, hardly soluble in alcohols and insoluble in ether, benzene and chloroform. It was found that the melting point is 204° to 205° C. and the specific optical rotation $[\alpha]_D^{24}$ is 45° (in water).

What is claimed is:

1. Process for the preparation of the compound 2-hydroxymethyl-3,4,5-trihydroxypiperidine which comprises culturing a 2-hydroxymethyl-3,4,5-trihydroxypiperidine-producing strain of the genus Streptomyces in the presence of a carbon source and nitrogen source until substantial production of said compound has occurred and isolating said compound from the culture medium.

2. The process according to claim 1 wherein said Streptomyces is *Streptomyces lavendulae* FERM 4301.

3. The process according to claim 1 wherein said culturing is conducted under submerged agitation conditions.

4. The process according to claim 1 wherein said isolation is effected by chromatographic or ion exchange fractionation.

* * * * *